United States Patent
Neumann

(10) Patent No.: US 11,232,259 B1
(45) Date of Patent: Jan. 25, 2022

(54) METHODS AND SYSTEMS FOR PERSONAL RECIPE GENERATION

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 0 days.

(21) Appl. No.: 17/106,793

(22) Filed: Nov. 30, 2020

(51) Int. Cl.
*G06F 17/00* (2019.01)
*G06F 40/284* (2020.01)
*G06F 40/30* (2020.01)
*G06F 16/9035* (2019.01)
*G16H 20/60* (2018.01)
*G06F 40/237* (2020.01)

(52) U.S. Cl.
CPC ........ *G06F 40/284* (2020.01); *G06F 16/9035* (2019.01); *G06F 40/237* (2020.01); *G06F 40/30* (2020.01); *G16H 20/60* (2018.01)

(58) Field of Classification Search
CPC ............. G06Q 10/101; G06Q 30/0282; G06Q 30/0278; G06Q 30/0631; G06N 20/00; G06N 7/005; G06F 16/337; G06F 16/284; G06F 16/951; G06F 16/3347; G06F 16/338; G06F 40/295; G06F 40/30; G06F 16/00; G06F 16/3329; G06F 40/205; G06F 40/279; G06F 40/56; G06F 16/258; G06F 16/906; G06F 16/908; G06F 40/20; G16H 20/60; G06K 2209/17; G09B 19/0092; G10L 15/1822
See application file for complete search history.

(56) References Cited

U.S. PATENT DOCUMENTS

| | | | |
|---|---|---|---|
| 10,720,235 B2 | 7/2020 | Leifer et al. | |
| 10,769,377 B2 | 9/2020 | Byron et al. | |
| 2009/0148818 A1* | 6/2009 | Li | G09B 19/0092 434/127 |
| 2013/0224694 A1* | 8/2013 | Moore | G16H 20/60 434/127 |

(Continued)

FOREIGN PATENT DOCUMENTS

WO WO-2016065463 A1 * 5/2016 ............. G16H 20/60

OTHER PUBLICATIONS

G. Ispirova, T. Eftimov and B. K. Seljak, "Comparing Semantic and Nutrient Value Similarities of Recipes," 2019 IEEE International Conference on Big Data (Big Data), Los Angeles, CA, USA, 2019, pp. 5131-5139, doi: 10.1109/BigData47090.2019.9006080. (Year: 2019).*

(Continued)

*Primary Examiner* — Michael Ortiz-Sanchez
(74) *Attorney, Agent, or Firm* — Caldwell Intellectual Property Law, LLC

(57) ABSTRACT

A system for personal recipe generation, the system including a computing device, the computing device configured to receive a target profile relating to a user, wherein the target profile identifies a nutrient target computed for a measured time interval; locate in a lexicon of ingredients, a first ingredient identifier including a first ingredient impact and a first semantic unit; compare the first ingredient impact to the target profile; and generate a personal recipe.

18 Claims, 9 Drawing Sheets

(56) References Cited

U.S. PATENT DOCUMENTS

| | | | |
|---|---|---|---|
| 2015/0161912 A1* | 6/2015 | Bhattacharjya | G06F 16/24578 434/127 |
| 2015/0170543 A1* | 6/2015 | Shahar | G09B 5/02 434/127 |
| 2015/0220624 A1* | 8/2015 | Bhatt | G06F 16/951 707/722 |
| 2016/0357942 A1* | 12/2016 | Wilkinson | G16H 20/60 |
| 2017/0139902 A1* | 5/2017 | Byron | G06Q 10/087 |
| 2017/0193853 A1* | 7/2017 | Byron | G09B 19/0092 |
| 2019/0171707 A1* | 6/2019 | Rapaport | G06N 3/08 |
| 2019/0286656 A1* | 9/2019 | Yerva | G16H 10/60 |
| 2019/0290172 A1* | 9/2019 | Hadad | A61B 5/0022 |
| 2021/0045682 A1* | 2/2021 | Poon | A61B 5/4866 |
| 2021/0050089 A1* | 2/2021 | Mohammed | G16H 15/00 |

OTHER PUBLICATIONS

Bodhisattwa Prasad Majumder, Shuyang Li, Jianmo Ni, and Julian McAuley. 2019. Generating Personalized Recipes from Historical User Preferences. In EMNLP. 5975-5981. (Year: 2019).*

* cited by examiner

| Target Profile A | Target Profile B | Ingredient Identifier | Serving | Ingredient Impact |
|---|---|---|---|---|
| Calcium: 1000 mg/day | Vitamin D: 5000 IU/day | Spinach, Raw | 1 cup | 30 mg calcium; 24 mg magnesium; 58 mcg folate |
| Iron: 27 mg/day | Vitamin C: 1000 mg/day | Spinach, Cooked | 1 cup | 244 mg calcium; 156 mg magnesium; 6 mg iron |
| Protein: 85 mg/day | Selenium: 80 mcg/day | Wild Alaskan Salmon | 4 ounces | 200 calories; 12 g fat; 32 mcg iodine; 81 mg choline |
| Fiber: 22 g/day | Zinc: 15 mg/day | Farm Raised Salmon | 4 ounces | 400 calories; 27 g fat; 12 mcg iodine; 14 mg choline |
| Folate: 800 mcg/day | Iodine: 600 mcg/day | Nori seaweed | 1/8 cup | 35 calories; 1 g fat; 40mg vitamin c; 5200 IU vitamin A |
| Zinc: 12 mg/day | Vitamin E: 400 IU/day | Celery, Raw | 1 medium stalk | 104 mg potassium; 32 mg sodium; 1 g sugar; 1 g fiber |

FIG. 7

METHODS AND SYSTEMS FOR PERSONAL RECIPE GENERATION

FIELD OF THE INVENTION

The present invention generally relates to the field of nourishment. In particular, the present invention is directed to methods and systems for personal recipe generation.

BACKGROUND

Personal recipe generation can be challenging. Knowing what nutrients and quantities of nutrients individually is difficult to ascertain.

SUMMARY OF THE DISCLOSURE

In an aspect, a system for personal recipe generation, the system comprising a computing device, the computing device designed and configured to receive a target profile relating to a user, wherein the target profile identifies a nutrient target computed for a measured time interval; locate, in a lexicon of ingredients, wherein the lexicon associates a plurality of ingredient identifiers to a plurality of ingredient impacts and a plurality of semantic units, a first ingredient identifier including a first ingredient impact and a first semantic unit; compare the first ingredient impact to the target profile; and generate a personal recipe, wherein generating the personal recipe further comprises locating, in the lexicon, a second ingredient identifier wherein the second ingredient identifier includes a second ingredient impact and a second semantic unit; comparing the second ingredient impact to the first ingredient impact and the target profile; and generating the personal recipe as a function of the first semantic unit and the second semantic unit.

In an aspect, a method of personal recipe generation, the method comprising receiving, by a computing device, a target profile relating to a user, wherein the target profile identifies a nutrient target computed for a measured time interval; locating, by the computing device, in a lexicon of ingredients, wherein the lexicon associates a plurality of ingredient identifiers to a plurality of ingredient impacts and a plurality of semantic units, a first ingredient identifier including a first ingredient impact and a first semantic unit; comparing, by the computing device, the first ingredient impact to the target profile; and generating, by the computing device, a personal recipe, wherein generating the personal recipe further comprises locating in the lexicon, a second ingredient identifier, wherein the second ingredient identifier includes a second ingredient impact and a second semantic unit; comparing the second ingredient impact to the first ingredient impact and the target profile; and generating the personal recipe as a function of the first semantic unit and the second semantic unit.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 7 is a diagrammatic representation of a target profile;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for a system for personal recipe generation. In an embodiment, a first ingredient identifier containing a first ingredient impact is compared to a target profile. A target profile may be generated utilizing information pertaining to a user to identify a nutrient target computed for a measured time interval. A personal recipe is then generated taking into account user specific needs, adjustments, and customization.

Figure 1:
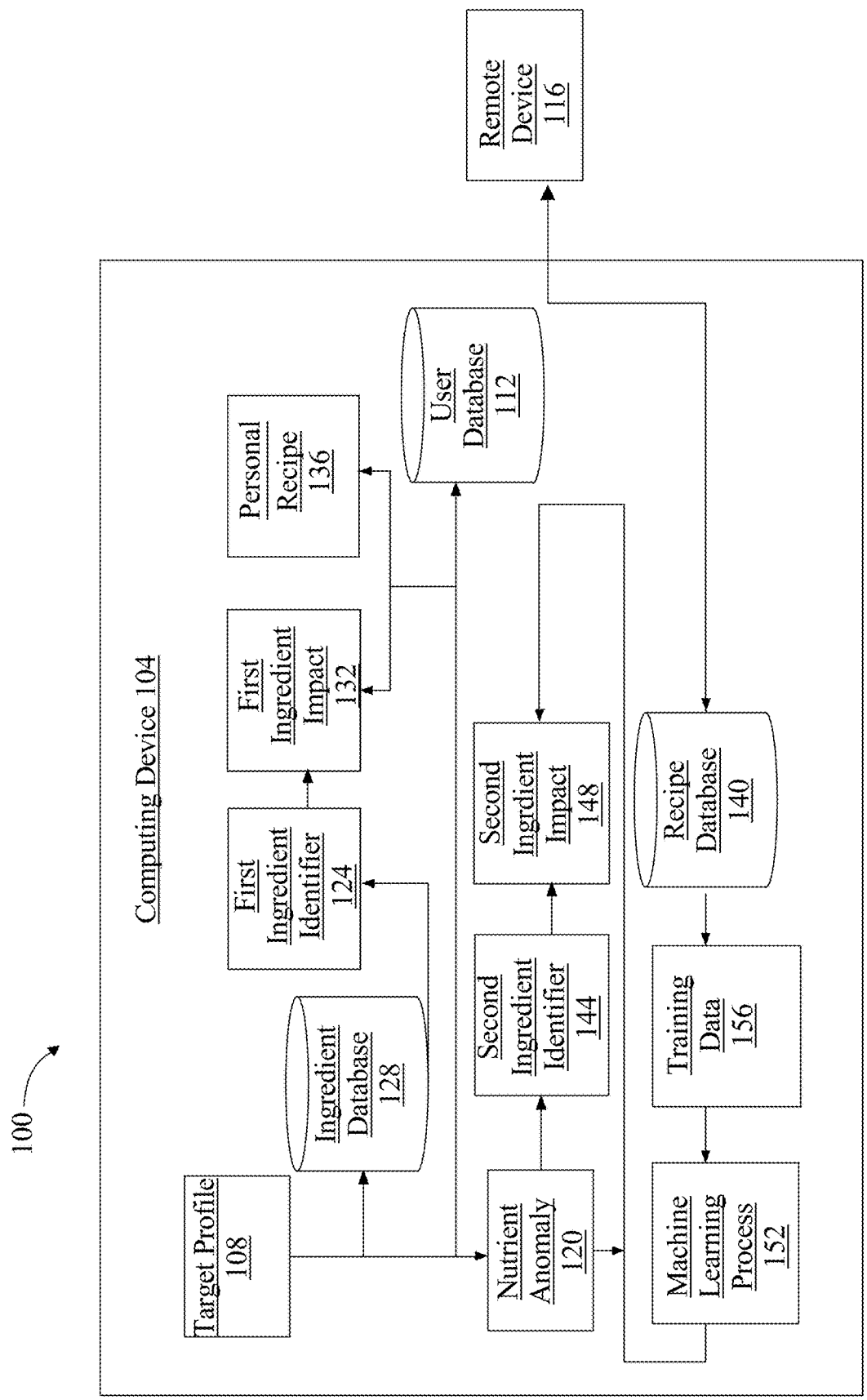
FIG. 1 is a block diagram illustrating an exemplary embodiment of a system for personal recipe generation.

Referring now to FIG. 1, an exemplary embodiment of a system 100 for personal recipe generation is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. computing device 104 may distribute one or more computing tasks as described below across a plurality of computing devices of computing device, which may operate in parallel, in series, redundantly, or in any other manner used for distribution of tasks or memory between computing devices. computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to receive a target profile 108 relating to a user. A "target profile," as used in this disclosure, is a recommended nutrient intake for a living subject, such as a human being and/or an animal. A "nutrient," as used in this disclosure, is a substance that provides nourishment essential for growth and/or maintenance of life for a living subject. A nutrient may include for example, protein, carbohydrates, fats, lipids, vitamins, minerals, trace minerals, water, and the like. A target profile 108 may a nutrient target computed for a measured time interval. A "nutrient target," as used in this disclosure, is a specified target of one or more recommended nutrients that the user is recommended to consume. A nutrient target may include a measured time interval, whereby the nutrient target may contain a recommended dose and/or time limit for consumption. For instance and without limitation, a target profile 108 may contain a recommended nutrient intake for a user who is a thirty seven year old pregnant female which contains nutrient recommendations such as 1000 micrograms of folate per day, and 1200 milligrams of calcium per day. In yet another non-limiting example, a target profile 108 may contain a recommended nutrient intake for a user who is a sixty two year old male which contains nutrient recommendations such as twenty five grams of fiber per day, 1 milligram of Vitamin B12 per day, and fifty six grams of protein each day. In an embodiment, a target profile 108 may identify a nutrient target computed for a measured time interval. For example, a target profile 108 may contain a recommended nutrient target over a certain period of time such as a recommendation per hour, per day, per week, per month, and the like. In an embodiment, a measured time internal may include a custom dosing schedule, such as a recommendation for a user to consume a dose of Vitamin C three times per day. In an embodiment, a measured time internal may include a dosing schedule such as once in the morning at 6:00 am and once in the evening at 6:00 pm. In an embodiment, target profile 108 may contain information pertaining to previous meal choices and/or selections that a user may have consumed and/or ordered. Such information may be retrieved from user database 112.

With continued reference to FIG. 1, information pertaining to a target profile 108 may be contained within user database 112. User database 112 may be implemented, without limitation, as a relational database, a key-value retrieval datastore such as a NOSQL database, or any other format or structure for use as a datastore that a person skilled in the art would recognized as suitable upon review of the entirety of this disclosure. User database 112 may include information pertaining to a user and/or a user's lifestyle that may be utilized to generate a target profile 108. For instance and without limitation, user database 112 may contain information that includes a user's current eating habits, allergies, food likes, food dislikes, activity levels, medical records, medical conditions and the like, as described below in more detail. Information contained within user database 112 may be stored within computing device 104, and/or received from remote device 116. Remote device 116 may contain any additional computing device, such as a mobile device, laptop, desktop, computer, and the like. Remote device 116 may receive information pertaining to a user and store the information pertaining to the user within user database 112 utilizing any network methodology as described herein.

With continued reference to FIG. 1, computing device 104 is configured to identify a nutrient anomaly 120 relating to a user and determine a target profile 108 utilizing the nutrient anomaly 120. A "nutrient anomaly," as used in this disclosure, is an abnormality relating to a user's current nutrient status and/or requirements. A nutrient anomaly 120 may include a nutrient deficiency and/or a nutrient excess. A "nutrient deficiency," as used in this disclosure, is a lack or shortage of one or more nutrients. A nutrient deficiency may occur due to various behaviors and/or factors that may affect a user, such as for example inadequate intake, altered absorption, increased requirement, increased losses, and/or altered metabolism. For instance, and without limitation, a menstruating female may be deficient in iron due to an increased loss of blood during monthly menstruations. In yet another non-limiting example, an alcoholic may be deficient in Vitamin B1 due to excess consumption of alcohol which may decrease levels of B vitamins. A "nutrient excess," as used in this disclosure, is an excess of a nutrient. A nutrient excess may occur due to various factors that may include for example improper intake, improper supplementation, malfunctioning of neuroendocrine system, toxins, drugs, and the like. For example, a nutrient excess may occur in a teenager who may consume an excess quantity of carbohydrates. A nutrient anomaly 120 may be self-reported by a user, such as a user who is a diabetic and who may self-report a nutrient anomaly 120 recommending the user to consume no more than 40 grams of carbohydrates at each meal. A nutrient anomaly 120 may be identified by computing device 104 based on information and/or medical records that may be contained within user database 112. For instance, and without limitation, information pertaining to a user and stored within user database 112 may specify that a user is currently taking a statin medication to lower the user's cholesterol levels. In such an instance, computing device 104 may detect a nutrient anomaly that specifies that the user requires an additional dose of co-enzyme q10, due to a nutrient deficiency exacerbated by statin medication intake. Computing device 104 may determine a target profile 108 using a nutrient anomaly 120. A nutrient anomaly 120 may contain a temporal element. A "temporal element," as used in this disclosure, is any information relating to time. A temporal element may specify how long a nutrient anomaly 120 has occurred. A temporal element may specify how long a nutrient anomaly 120 may impact a target profile 108. For instance, and without limitation, a nutrient anomaly 120 such as a user with a ferritin level of 5 micrograms per liter may contain a temporal element indicating that the user will require extra intake of iron for at least six months. In yet another non-limiting example, a nutrient anomaly 120 such as a user with colitis may contain a temporal element indicating that the user will require 5 grams per day of soluble fiber for the duration of colitis.

With continued reference to FIG. 1, a first nutrient anomaly may be identified as a function of a second nutrient anomaly. This may occur for example, such as where a first nutrient deficiency and/or excess may cause a deficiency and/or excess of a second nutrient deficiency. For instance, and without limitation, a first nutrient anomaly such as a zinc deficiency may cause a subsequent deficiency of a second nutrient anomaly such as copper. This may also occur such as where the replenishment of a first nutrient anomaly requires the replenishment of a second nutrient anomaly. For instance, and without limitation, the replenishment of a first nutrient anomaly such as Vitamin B1 or thiamine may require the replenishment of a second nutrient anomaly such as Vitamin B2 or riboflavin. This may also occur such as where a first nutrient anomaly may be related to a second nutrient anomaly. For instance, and without limitation, a first nutrient anomaly such as an iron deficiency may be related to a second nutrient anomaly such as a ferritin deficiency. In yet another non-limiting example, a first nutrient anomaly such as a selenium deficiency may be related to a second nutrient anomaly such as an iodine deficiency.

With continued reference to FIG. 1, computing device 104 is configured to locate in a lexicon of ingredients wherein the lexicon associates a plurality of ingredient identifiers to a plurality of ingredient impacts and a plurality of semantic units, a first ingredient identifier including a first ingredient impact and a first semantic unit. An "ingredient identifier," as used in this disclosure, is a unique sequence of characters and/or numerical values, used to identify an ingredient. An "ingredient," as used in this disclosure, is any food, beverage, meal, snack, and/or substance that may be combined to make a particular dish and/or meal. An ingredient may include for example, a vegetable such as an artichoke or a fruit such as an apple. An ingredient may include for example, a protein source such as poultry, eggs, nuts, fish, beans, meat, tofu, seitan, and the like. An ingredient may include a grain such as bread, cereal, rice, pasta, millet, and the like. An ingredient may include beverages such as cow's milk or non-dairy alternatives such as coconut milk or soy milk. An ingredient may include an oil such as olive oil or coconut oil. An ingredient may include a baking essential such as brown sugar or soy sauce. A "lexicon," as used in this disclosure, is any data structure suitable for use as user database 112 as described above. A "semantic unit," as used in this disclosure, is any textual data. A semantic unit may contain information describing a category and/or class of a first ingredient identifier. For example, a semantic unit may indicate if a first ingredient identifier belongs to a category such as a vegetable, a fruit, a spice, a protein source, and the like. For instance, and without limitation, a first ingredient identifier such as a tomato may be associated with a semantic unit such as vegetable. In yet another non-limiting example, a first ingredient identifier such as filet mignon may be associated with a semantic unit such as animal protein. Information pertaining to semantic units may be updated in real time, utilizing any network methodology as described herein.

With continued reference to FIG. 1, a first ingredient identifier 124 contains a first ingredient impact 132. An "ingredient impact," as used in this disclosure, is data including any numerical, character, and/or symbolic data, describing nutrients contained within an ingredient. In an embodiment, nutrients contained within an ingredient may be based on one or more nutritional systems created and/or implemented by governments, non-profit organizations, private institutions, companies, and the like. For example, an ingredient impact 124 may indicate that an ingredient such as broccoli contains 10 grams of carbohydrates and 4 grams of fiber in a 150-gram serving. In yet another non-limiting example, an ingredient impact 124 may indicate that an ingredient such as wild caught salmon contains 23 grams of protein, 4 grams of fat, 85 milligrams of cholesterol, and 1200 milligrams of omega-3 fatty acids in a 4 ounce serving. Information pertaining to ingredient identifiers and/or ingredient impacts may be contained within ingredient database 128. In an embodiment, an ingredient impact may be determined using a user's biological extraction, which may indicate how well a user may absorb a particular nutrient, metabolize a certain ingredient, excrete a vitamin or mineral and the like. A "biological extraction," as used in this disclosure, is data indicative of a person's biological state; biological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, biological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various nourishments such as dehydration, nutrient deficiencies, anemia, and/or blood loss. Biological extraction data may alternatively or additionally include any data used as a biological extraction as described in U.S. Nonprovisional application Ser. No. 16/502,835, filed on Jul. 3, 2019, and entitled "METHODS AND SYSTEMS FOR ACHIEVING VIBRANT CONSTI- TUTION BASED ON USER INPUTS," the entirety of which is incorporated herein by reference.

With continued reference to FIG. 1, computing device 104 may locate a first ingredient identifier 124 based on a user preference. A "user preference," as used in this disclosure, is an affinity and/or dislike for one or more ingredients. For example, a user preference may indicate that a user enjoys protein sources that include chicken, beef, and fish, and that the user dislikes protein sources that include eggs, tofu, and pork. In yet another non-limiting example, a user preference may indicate that a user does not consume animal containing products because of ethical concerns. A user preference may highlight eating patterns of a user, including how many meals per day the user typically consumes, what types of foods and ingredients the user enjoys consuming, what types of foods and ingredients the user dislikes, any allergies the user has, and/or ingredients the user may abstain from consuming due to ethical and/or religious beliefs. Information pertaining to a user preference may be stored within user database 112. In an embodiment, information pertaining to a user preference may be collected from a user using a questionnaire and/or series of questions to prompt a user for information. Such information may be collected utilizing remote device 116 and/or any network methodology as described herein. Computing device 104 may utilize a user preference to locate a first ingredient identifier 124. For example, a user preference that indicates a user dislikes shellfish, may be utilized to select a first ingredient identifier 124 that contains a different fish option, such as tuna or swordfish. In yet another non-limiting example, a user preference that indicates a user likes oranges may be utilized to select other ingredients that contain citrus fruits such as grapefruit, line, lemon, kumquat, clementine, tangelo, and the like. In an embodiment, computing device 104 may identify a first ingredient identifier 124 based on a user preference, utilizing model known as a classifier. A "classifier," as used in this disclosure, is a process whereby computing device 104 derives from training data, a model known as a "classifier" for sorting inputs into categories or bins of data. Classification algorithms may include linear classifiers such as logistic regression, Naïve Bayes classification, Fisher's linear discriminant, k-nearest neighbors, support vector machines, quadratic classifiers, Kernel estimation, decision trees, boosted trees, random forest, neural networks, and the like. Classification may be performed as described in U.S. Nonprovisional application Ser. No. 16/887,388, filed on May 29, 2020, and entitled "METHODS, SYSTEMS, AND DEVICES FOR GENERATING A REFRESHMENT INSTRUCTION SET BASED ON INDIVIDUAL PREFERENCES," the entirety of which is incorporated herein by reference.

With continued reference to FIG. 1, computing device 104 is configured to compare first ingredient impact 132 to target profile 108. Comparing may include determining how well first ingredient impact 132 meets the needs and/or requirements of a user as specified within target profile 108. For instance, and without limitation, target profile 108 may specify that a user requires 60 grams of protein per day. In such an instance, computing device 104 may compare the 60 gram of protein per day requirement to first ingredient impact 132, which may specify that an ingredient such as one tablespoon of almond butter contains 4 grams of protein. Computing device 104 may accept and/or reject first ingredient identifier 124, based on the comparison. For instance and without limitation, a target profile 108 that specifies a user requires 10,000 milligrams of Vitamin C per day may be compared to first ingredient impact 132 which specifies that an ingredient such as an apple contains 80 milligrams of Vitamin C per serving, which may be rejected, in contrast to an ingredient such as guava which contains 600 milligrams of Vitamin C per serving. Comparing may include evaluating a temporal element of a nutrient anomaly, to determine a dose and/or quantity of an ingredient that may meet requirements contained within target profile 108. For instance and without limitation, a nutrient anomaly that contains a temporal element indicating that a user requires 15 grams of extra protein each day for the next three weeks while training for a marathon, may be utilized by computing device 104 to select and/or compare a first ingredient impact 132 that contains a higher dose of protein per serving as compared to a first ingredient impact 132 that contains a lower dose of protein per serving. In such an instance, computing device 104 may compare an ingredient such as tofu containing 20 grams of protein per serving to a target profile 108 requiring the user to consume a minimum of 15 grams of protein three times per day. Comparing may include determining by computing device 104 what serving size and/or portion of first ingredient identifier 124 may be recommended for a user based on a user's target profile 108. For instance and without limitation, comparing may include determining that a first ingredient identifier 124 may meet a user's nutritional targets contained within target profile 108 at a serving size of six ounces, however the first ingredient identifier 124 may not meet a user's target profile 108 at a larger serving size, and as such may even be determinantal to a user's health at a larger portion size. For instance and without limitation, a target profile 108 may specify that a user is to consume no more than 12 grams of mannitol per day, and as such, computing device 104 may suggest that a user is allowed no more than a serving size of 4 button mushrooms per day, because button mushrooms contain high quantities of mannitol. In such an instance, computing device 104 may recommend a user to avoid other ingredient identifiers that contain high levels of mannitol, including for example, celery, olives, onion, and pumpkin.

With continued reference to FIG. 1, computing device 104 is configured to generate a personal recipe 136. A "personal recipe," as used in this disclosure, is a custom set of instructions for preparing a particular dish, which may include a list of ingredients and/or quantities of ingredients to be utilized to prepare the particular dish. A personal recipe 136 may be customized and/or optimized for each individual user. Personal recipe 136 may be generated as a function of first semantic unit and second semantic unit. This may be performed utilizing language processing as described below in more detail. Customization may include adjusting ingredients, ingredient quantities, cooking styles, and the like based on a user's target profile 108 and/or other individual and custom information relating to a user. In an embodiment, such information utilized to create and/or customize a personal recipe may be contained within ingredient database 128 and/or user database 112. For instance, and without limitation, a personal recipe 136 for a first user with a target profile 108 specifying that a user is allowed to consume no more than 1000 milligrams of sodium per day may be used to customize a personal recipe 136 for shrimp stir fry to adjust a quantity of a first ingredient identifier 124 containing soy sauce to be reduced to use no more than 1 tablespoon of low sodium soy sauce, as compared to a user profile 108 that does not contain a restriction on sodium, whereby the personal recipe 136 for shrimp stir fry may call for 2 tablespoons of regular soy sauce. Information pertaining to personal recipes 136 may be contained within recipe database 140. Recipe database may be implemented as any data structure suitable for use as user database 112 as described above in more detail. Generating a personal recipe 136 may include selecting a cooking style. A "cooking style," as used in this disclosure, is a method of preparing a recipe. A cooking style may identify one or more styles such as grilling, steaming, baking, roasting, poaching, braising, boiling, searing, simmering, frying, barbequing, brining, basting, charbroiling, deglazing, marinating, pan frying, sauteing, stewing, and the like. In an embodiment, a personal recipe 136 may identify one or more cooking styles. For example, a personal recipe 136 for flank steak may include marinating the steak followed by grilling the steak. Computing device 104 may select a cooking style using target profile 108. Computing device 104 may utilize information contained within ingredient database 128

With continued reference to FIG. 1, computing device 104 may generate personal recipe 136 by locating a second ingredient identifier 144. A second ingredient identifier 144 may include any ingredient suitable for use as first ingredient identifier 124 as described above in more detail. A second ingredient identifier 144 contains a second ingredient impact 148. A second ingredient impact 148 includes any ingredient impact suitable for use as first ingredient impact 132 as described above in more detail. In an embodiment, a second ingredient identifier 144 may be located using first ingredient identifier 124. In an embodiment, a first ingredient identifier 124 may be best suited to be matched and prepared in combination with a second ingredient identifier 144. For example, a first ingredient such as wild salmon may be best prepared in combination with a second ingredient such as lemon, while a first ingredient such as mahi mahi may be best prepared in combination with a second ingredient such as coconut. Information pertaining to palatability and ingredient combinations may be best stored within recipe database 140. In an embodiment, information pertaining to which ingredients may be substituted for one another due to allergies, intolerances, dislikes and the like may be stored and contained within ingredient database 128. For example, information contained within ingredient database 128 may specify that a first ingredient such as fresh parsley may be substituted with basil, oregano, and/or chives such as when a user cannot consume parsley and/or if parsley may adversely affect a target profile 108. Second ingredient identifier 144 includes a second semantic unit. Second semantic unit may include any textual data suitable for use as first semantic unit as described above in more detail. Computing device 104 may locate a second ingredient identifier 144 by locating an ingredient that may improve a first ingredient impact 132. An ingredient may improve a first ingredient impact 132, such as when an ingredient may improve the nutrient profile of a first ingredient identifier 124 such as by impacting nutrient bioavailability, nutrient density, quantity and variety of nutrients, nutrient absorption and the like. Information pertaining to how an ingredient may improve a first ingredient impact 132 may be stored and contained within ingredient database 128. For instance, and without limitation, an ingredient such as olive oil may improve a first ingredient impact 132 of a tomato, whereby olive oil may boost absorption of lycopene contained within the tomato. In yet another non-limiting example, an ingredient such as avocado may improve a first ingredient impact 132 of leafy greens whereby monounsaturated fat found in an avocado may increase absorption and bioavailability of phytochemicals contained within leafy greens. Computing device 104 may determine that an ingredient may improve a first ingredient impact 132 such as by retrieving information that may be contained within ingredient database 128.

In yet another non-limiting example, computing device 104 may determine how a particular ingredient such as a second ingredient identifier 144 may impact and/or improve a first ingredient impact 132 such as by using a machine-learning process, including any of the machine-learning processes as described herein. For instance and without limitation, computing device 104 may utilize a plurality of ingredients and first ingredient identifier 124 and first ingredient impact 132 as inputs to a machine-learning process and output which ingredients from the plurality of input ingredients are able to improve first ingredient impact 132. This may be performed, utilizing any methodology as described herein.

With continued reference to FIG. 1, computing device 104 is configured to compare second ingredient impact 148 to first ingredient impact 132 and target profile 108. For instance and without limitation, computing device 104 may compare a second ingredient impact 148 for an ingredient such as kale to see how the second ingredient impact 148 may compare to and/or affect a first ingredient impact 132 for an ingredient such as chicken. In such an instance, computing device 104 may evaluate first ingredient impact 132 and second ingredient impact 148 in comparison to target profile 108, to determine how each ingredient impact will affect target profile 108. For instance and without limitation, a first ingredient such as a wild salmon may be compared to a second ingredient such as sweet potato and whereby both ingredients are compared to a target profile 108, to determine how each ingredient alone and/or in combination may affect each ingredient impact and/or impact target profile 108. Computing device 104 generates a personal recipe 136 as a function of first ingredient impact 132 and second ingredient impact 148.

With continued reference to FIG. 1, computing device 104 may generate personal recipe 136 using a machine learning process 152. A "machine learning process," as used in this disclosure, is a process that automatically uses training data 156 to generate an algorithm that will be performed by computing device 104 to produce outputs such as personal recipe 136 given data provided as inputs such as target profile 108; this is in contrast to a non-machine learning software program where the commands to be executed are determined in advance by a user and written in a programming language.

Still referring to FIG. 1, "training data," as used herein, is data containing correlations that a machine-learning process may use to model relationships between two or more categories of data elements. For instance, and without limitation, training data 156 may include a plurality of data entries, each entry representing a set of data elements that were recorded, received, and/or generated together; data elements may be correlated by shared existence in a given data entry, by proximity in a given data entry, or the like. Multiple data entries in training data 156 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 156 according to various correlations; correlations may indicate causative and/or predictive links between categories of data elements, which may be modeled as relationships such as mathematical relationships by machine-learning processes as described in further detail below. Training data 156 may be formatted and/or organized by categories of data elements, for instance by associating data elements with one or more descriptors corresponding to categories of data elements. As a non-limiting example, training data 156 may include data entered in standardized forms by persons or processes, such that entry of a given data element in a given field in a form may be mapped to one or more descriptors of categories. Elements in training data 156 may be linked to descriptors of categories by tags, tokens, or other data elements; for instance, and without limitation, training data 156 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 1, training data 156 may include one or more elements that are not categorized; that is, training data 156 may not be formatted or contain descriptors for some elements of data. Machine-learning algorithms and/or other processes may sort training data 156 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 156 to be made applicable for two or more distinct machine-learning algorithms as described in further detail below. Training data 156 used by machine learning process 152 may correlate any input data as described in this disclosure to any output data as described in this disclosure. As a non-limiting illustrative example an input such as a target profile 108 may be correlated to an output such as personal recipe 136. In yet another non-limiting example, an input such as a first ingredient impact 132 may be correlated to an output such as personal recipe 136.

With continued reference to FIG. 1, personal recipe 136 is generated as a function of first semantic unit and second semantic unit. In an embodiment, this may be performed utilizing a language processing module. Language processing module may be configured to extract, from the one or more documents, one or more words. One or more words may include, without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module may compare extracted words to categories of physiological data recorded at diagnostic engine, one or more prognostic labels recorded at diagnostic engine, and/or one or more categories of prognostic labels recorded at diagnostic engine; such data for comparison may be entered on diagnostic engine as described above using expert data inputs or the like. In an embodiment, one or more categories may be enumerated, to find total count of mentions in such documents. Alternatively, or additionally, language processing module may operate to produce a language processing model. Language processing model may include a program automatically generated by computing device and/or language processing module to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like.

Still referring to 1, language processing module and/or diagnostic engine may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module may use a corpus of documents to generate associations between language elements in a language processing module, and diagnostic engine may then use such associations to analyze words extracted from one or more documents and determine that the one or more documents indicate significance of a category. In an embodiment, diagnostic engine may perform this analysis using a selected set of significant documents, such as documents identified by one or more experts as representing good information; experts may identify or enter such documents via graphical user interface, or may communicate identities of significant documents according to any other suitable method of electronic communication, or by providing such identity to other persons who may enter such identifications into diagnostic engine. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine may automatically obtain the document using such an identifier, for instance by submitting a request to a database or compendium of documents such as JSTOR as provided by Ithaka Harbors, Inc. of New York.

Figure 2:
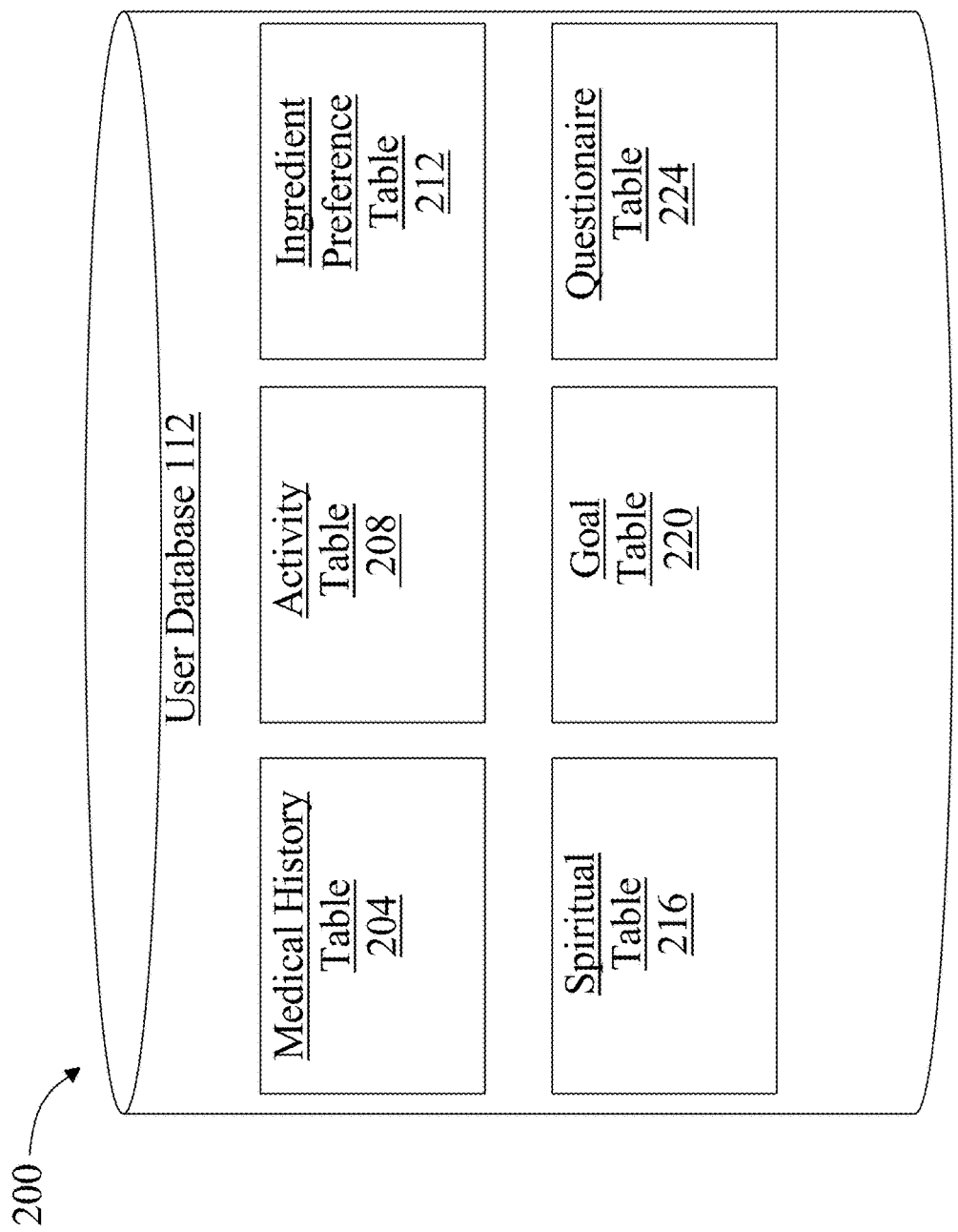
FIG. 2 is a block diagram illustrating an exemplary embodiment of a user database.

Referring now to FIG. 2, an exemplary embodiment 200 of user database 112 is illustrated. User database 112 may be implemented as any data structure suitable for use as described above in more detail in reference to FIG. 1. One or more tables contained within user database 112 may include medical history table 204; medical history table 204 may include any information pertaining to a user's medical history. For instance, and without limitation, medical history table 204 may include an entry describing a chronic medical condition that the user may suffer from, such as rheumatoid arthritis. One or more tables contained within user database 112 may include activity table 208; activity table 208 may include any information relating to physical activity that the user may engage in. For instance, and without limitation, activity table 208 may describe a user's exercise routine, whereby the user may engage in strength training two days per week and cardiovascular exercise three days per week. One or more tables contained within user database 112 may include ingredient preference table 212; ingredient preference table 212 may include any information describing foods that a user likes, dislikes, avoids, abstains from consuming and the like. For instance, and without limitation, ingredient preference table 212 may specify that a user does not consume pork containing products for religious reasons. One or more tables contained within user database 112 may include spiritual table 216; spiritual table 216 may include any information describing a user's spiritual practice. For instance, and without limitation, spiritual table 216 may specify that a user engages in a meditation practice three days per week for fifteen minutes. One or more tables contained within user database 112 may include goal table 220; goal table 220 may include information describing any personal goals that a user seeks to achieve. For instance, and without limitation, goal table 220 contain an entry describing a user's wellness related goal to lose fifteen pounds over the next three months. One or more tables contained within user database 112 may include questionnaire table 224; questionnaire table 224 may include information about a user, obtained from a questionnaire. For instance and without limitation, questionnaire table 224 may include answers to questions that specify the eating patterns of a user, including the time of day a user consumes meals, how many meals per day the user typically eats, and how many snacks per day the user eats.

Figure 3:
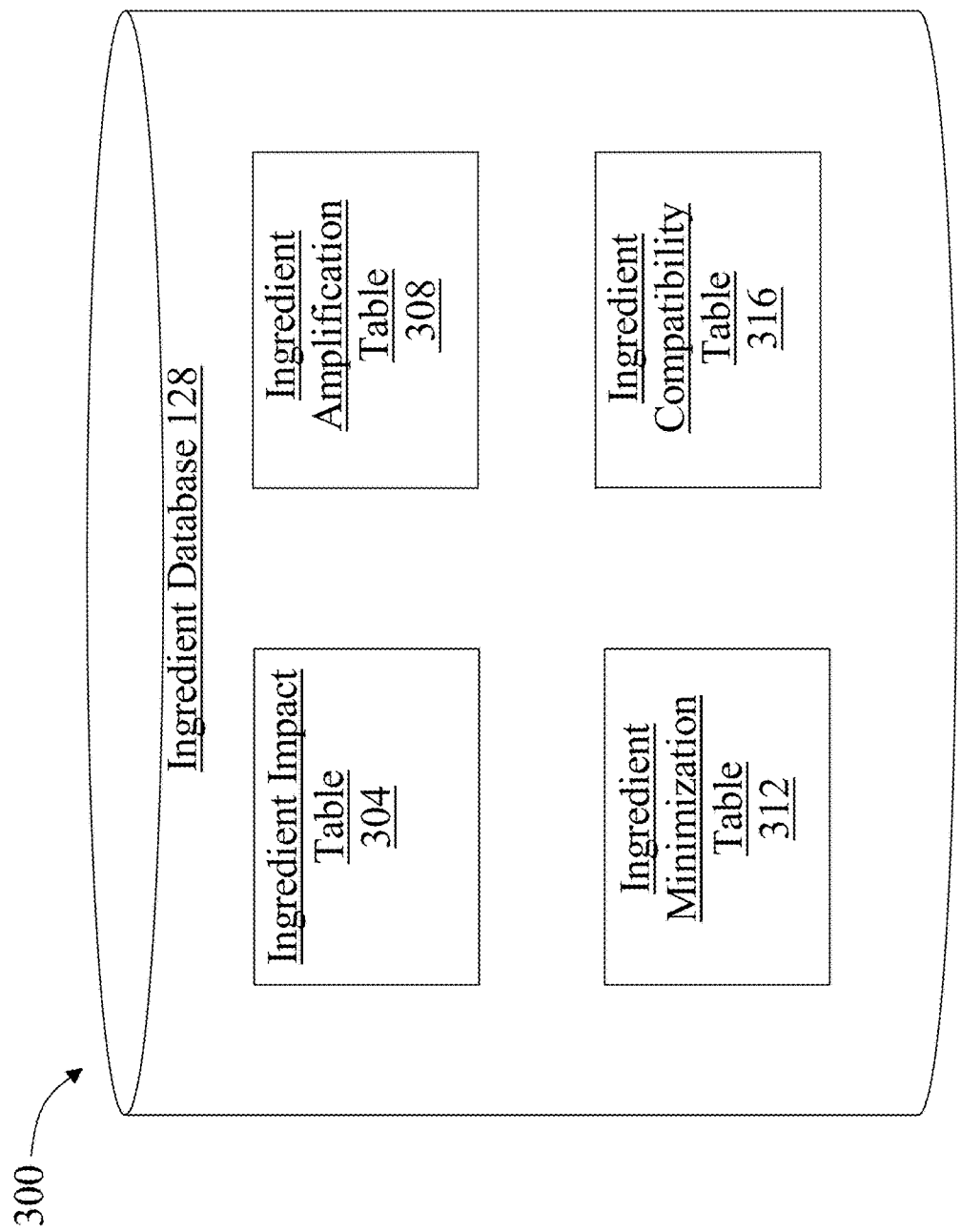
FIG. 3 is a block diagram illustrating an exemplary embodiment of an ingredient database.

Referring now to FIG. 3, an exemplary embodiment 300 of ingredient database 128 is illustrated. Ingredient database 128 may be implemented as any data structure suitable for use as user database 112 as described above in more detail in reference to FIG. 1. One or more tables contained within ingredient database 128 may include ingredient impact table 304; ingredient impact table 304 may contain information pertaining to ingredient impacts for various ingredients. One or more tables contained within ingredient database 128 may include ingredient amplification table 308; ingredient amplification table 308 may contain information describing ingredients that may amplify ingredient impacts of other ingredients. One or more tables contained within ingredient database 128 may include ingredient minimization table 312; ingredient minimization table 312 may contain information describing ingredients that may minimize ingredient impacts of other ingredients. One or more tables contained within ingredient database 128 may include ingredient compatibility table 316; ingredient compatibility table 316 may include information describing the compatibility of various ingredients.

Figure 4:
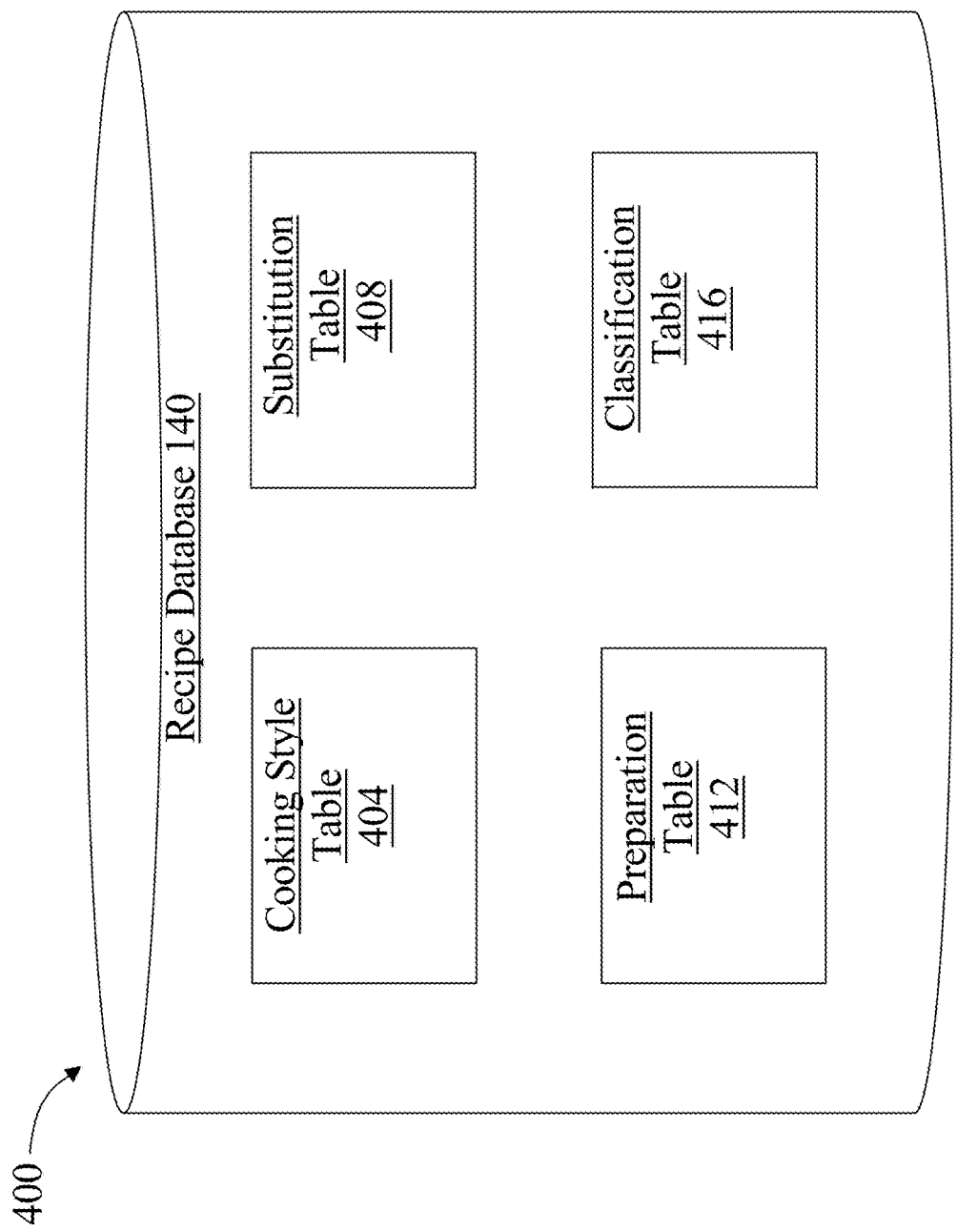
FIG. 4 is a block diagram illustrating an exemplary embodiment of a recipe database.

Referring now to FIG. 4, an exemplary embodiment 400 of recipe database 140 is illustrated. Recipe database 140 may be implemented as any data structure suitable for use as user database 112 as described above in more detail in reference to FIG. 1. One or more tables contained within recipe database 140 may include cooking style table 404; cooking style table 404 may contain information describing various cooking styles and/or cooking techniques that may be applied to various recipes. One or more tables contained within recipe database 140 may include substitution table 408; substitution table 408 may include information describing which ingredients can be substituted for one another in various recipes, due to allergies, dislikes, nutritional content, and the like. One or more tables contained within recipe database may include preparation table 412; preparation table 412 may include information describing various preparation techniques for recipes. One or more tables contained within recipe database 140 may include classification table 416; classification table 416 may contain information describing diets and/or styles of eating that a recipe may be suitable for.

Figure 5:
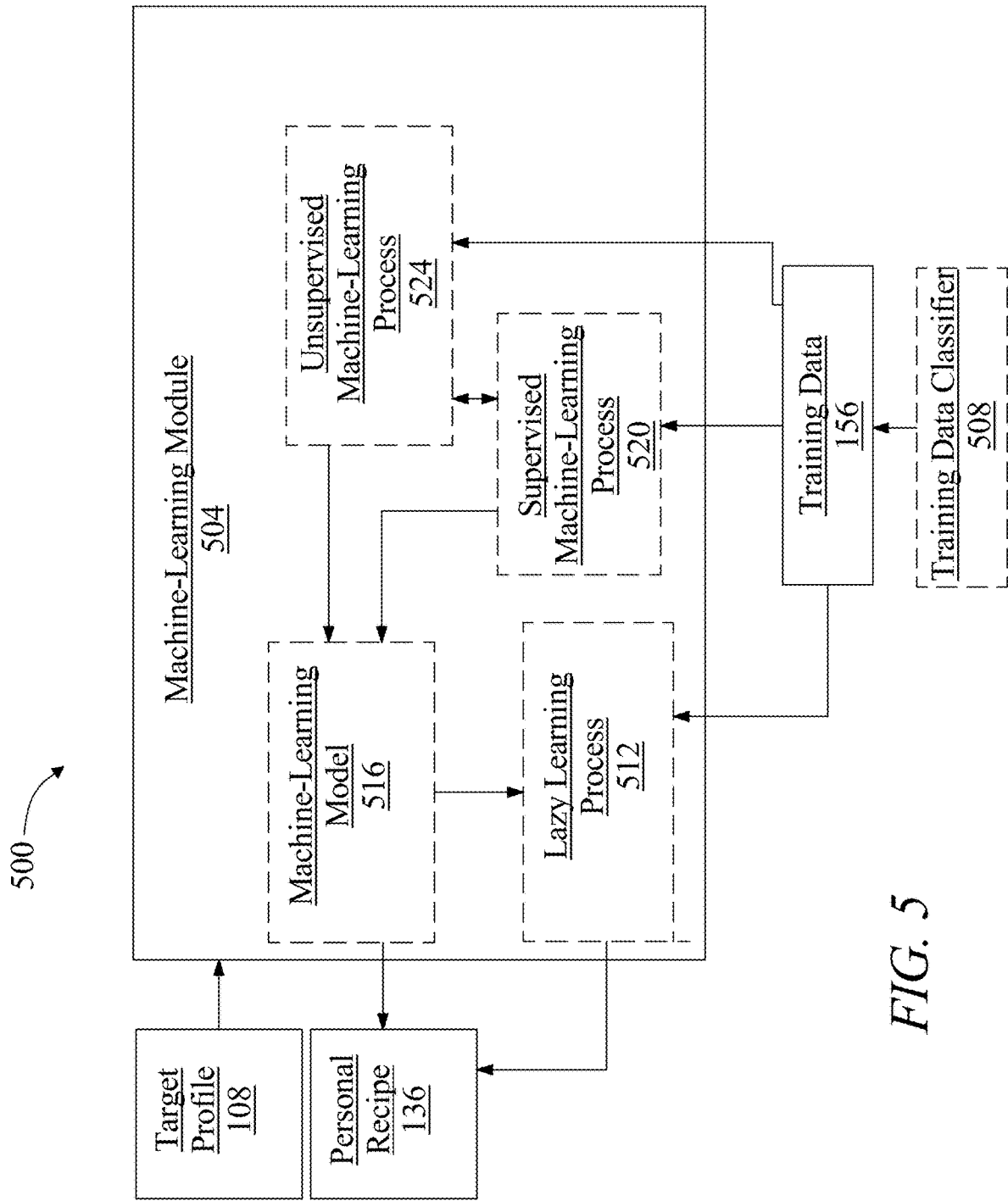
FIG. 5 is a flow diagram illustrating an exemplary embodiment of a machine learning module.

Referring now to FIG. 5, an exemplary embodiment of a machine-learning module 504 that may perform one or more machine-learning processes as described in this disclosure is illustrated. Machine-learning module may perform determinations, classification, and/or analysis steps, methods, processes, or the like as described in this disclosure using machine learning processes. Machine learning process 152 includes any of the machine learning processes as described above in more detail.

Further referring to FIG. 5, training data may be filtered, sorted, and/or selected using one or more supervised and/or unsupervised machine-learning processes and/or models as described in further detail below; such models may include without limitation a training data classifier 508. Training data classifier 508 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine learning process 152 may generate a classifier using a classification algorithm, defined as a process whereby a computing device and/or any module and/or component operating thereon derives a classifier from training data 156. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 508 may classify elements of training data to a subpopulation of various target profiles 108, such as those users who require additional quantities of certain nutrients and/or those users who require lower quantities of certain nutrients.

Still referring to FIG. 5, machine-learning module 504 may be configured to perform a lazy-learning process 512 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 156. Heuristic may include selecting some number of highest-ranking associations and/or training data 156 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively, or additionally, and with continued reference to FIG. 5, machine-learning processes as described in this disclosure may be used to generate machine-learning models 516. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 516 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 516 may be generated by creating an artificial neural network, such as a convolutional neural network comprising an input layer of nodes, one or more intermediate layers, and an output layer of nodes. Connections between nodes may be created via the process of "training" the network, in which elements from a training data 156 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 520. At least a supervised machine-learning process 520, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include target profile 108 as described above as inputs, personal recipe 136 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 156. Persons skilled in the art, upon reviewing the entirety of this disclosure, will be aware of various possible variations of at least a supervised machine-learning process 520 that may be used to determine relation between inputs and outputs. Supervised machine-learning processes may include classification algorithms as defined above.

Further referring to FIG. 5, machine learning processes may include at least an unsupervised machine-learning processes 524. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 504 may be designed and configured to create a machine-learning model 516 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
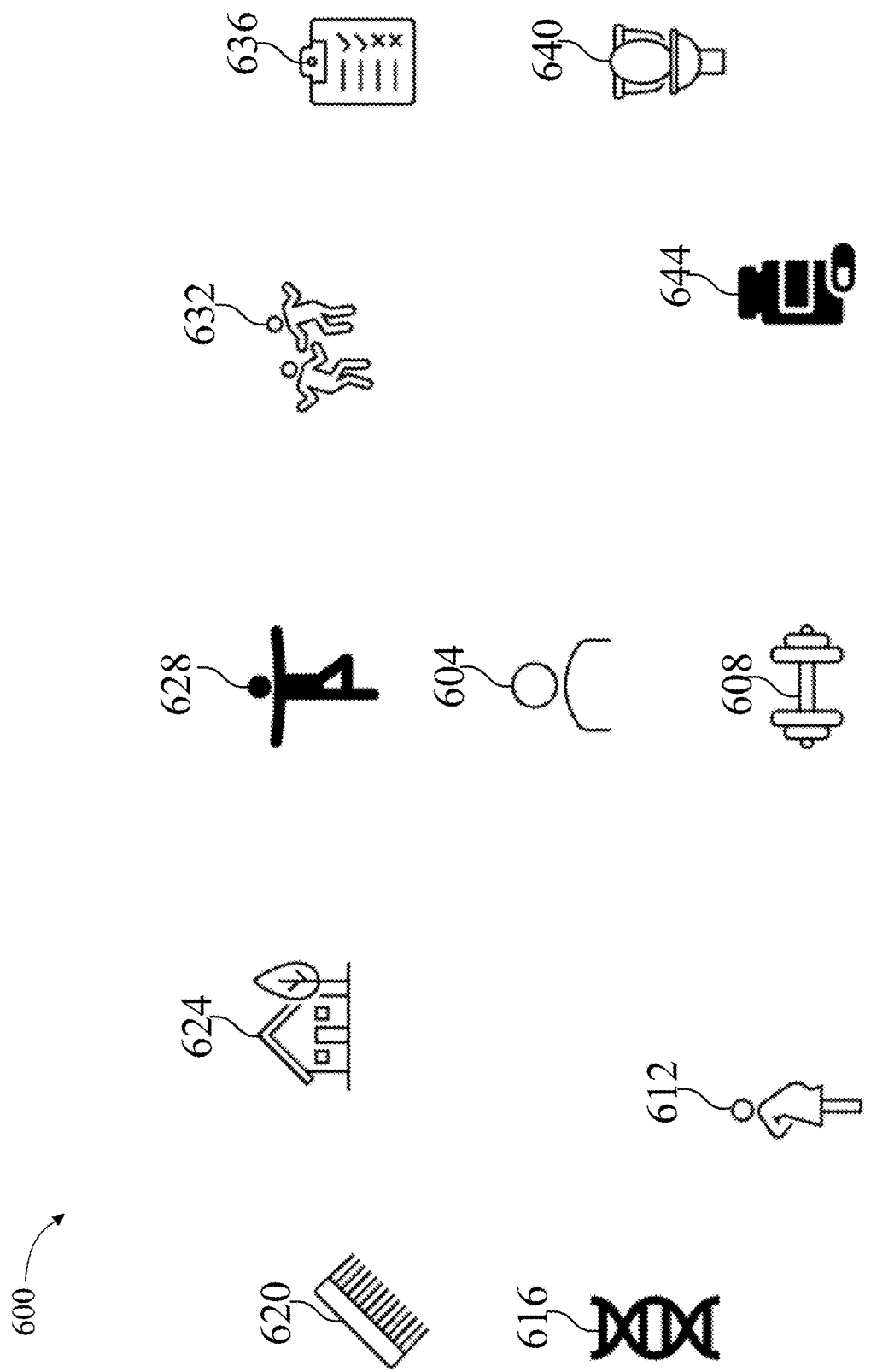
FIG. 6 is a diagrammatic representation of aspects of a user database.

Referring now to FIG. 6, an exemplary embodiment 600 of information contained within user database 112 is illustrated. One or more entries contained within user database 112 may be utilized to generate and/or calculate target profile 108. User database 112 may contain information pertaining to a user 604, such as a human being. Entries contained within user database 112 may include fitness entries 608 which may describe information any fitness habits of a user. For example, a user may indicate that the user lifts weights on Tuesday and Thursday mornings at 6:00 am. Entries contained within user database 112 may include life stage information 612 which may describe a particular life stage that a user is currently at. For example, a female user may indicate if the user is currently pregnant which may cause the user to have extra nutritional demands and needs. Entries contained within user database 112 may include genetic entries 616, which may include any genetic tests and/or genetic results pertaining to a user. For example, a user may have a breast cancer gene mutation such as a BRCA1 or BRCA2 mutation, which may be detected based on previous genetic testing and/or sequencing. Entries contained within user database 112 may include hygiene entries 620, which may include any hygiene habits and/or products that the user frequently engages in. For example, a user may specify that the user purchases and uses non-toxic shampoo and conditioner but utilizes conventional toothpaste and facewash. Entries contained within user database 112 may include balance entries 628. Balance entries 628 may include information describing how flexible a user is, how often a user practices and/or engages in balance exercise, and types of coordinated balance exercise the user may engage in. Entries contained within user database 112 may include relaxation entries 632. Relaxation entries 632 may include information describing what sorts of activities a user engages in during time off from work and/or school, such as dancing, meditation, recreational activities, group exercise, hobbies, and the like. Entries contained within user database 112 may include questionnaire entries 636. Questionnaire entries 636 may include information describing a user's response to one or more questionnaires about the user's lifestyle and/or habits. Entries contained within user database 112 may include elimination entries 640. For example, elimination entries 640 may include a description of a user's eliminations and/or any gastrointestinal problems the user may experience, such as diarrhea, constipation, gas, bloating, and the like. Entries contained within user database 112 may include medication entries 644. Medication entries 644 may include information describing any prescription medications, herbal remedies, supplements, homeopathic remedies and the like that the user may consume.

Referring now to FIG. 7, an exemplary embodiment 700 of target profiles and ingredient identifiers is illustrated. In an embodiment, target profile A 704 may be prepared and calculated for a user. In such an instance, target profile A 704 may contain one or more recommended nutrient intakes for a first user. For instance, and without limitation, target profile A 704 may recommend a user to consume 100 mg/day of calcium. In an embodiment, target profile A 704 may contain one or more recommend nutrient intakes for a specified period of time, such as the recommended intake per meal, per day, per week, and the like. In an embodiment, a period of time to report a recommended intake of a nutrient may be specified for the period of time as requested by a user, and/or a user preference contained within user database 112. In an embodiment, computing device 104 may calculate target profile B 708, which may contain one or more recommended nutrient intakes for a second user. In an embodiment, target profile A 704 may contain various nutrients and/or recommended doses which may be different from those contained within target profile B 708. For instance and without limitation, target profile A 704 may be generated for a first user who may be pregnant, and may require additional supplementation with nutrients such as calcium, iron, folate, and fiber whereas target profile B 708 may be generated for a second user who may not be pregnant and who may suffer from a medical condition such as hypothyroidism and may require recommended doses of nutrients such as selenium, zinc, and iodine. In an embodiment, an ingredient identifier 712 may specify the state of an ingredient, such as if an ingredient containing spinach is raw or cooked spinach or if fish includes wild caught fish or farmed fish. In an embodiment, a serving size 716 of an ingredient may be specified. In an embodiment, an ingredient impact 720 may contain the nutritional impact of one or more ingredients contained within an ingredient. For instance, and without limitation, the ingredient impact of raw spinach may specify that 1 cup of raw spinach may contain 30 mg calcium, 24 mg magnesium, and 58 mcg of folate. In an embodiment, computing device 104 may display nutrients contained within an ingredient impact that are most relevant and/or that match nutrients contained within a target profile. For example, a target profile that recommends a user to consume 15 mg of zinc per day may be utilized to locate the ingredient impact of an ingredient that contains zinc, whereas ingredients that do not contain zinc may not be selected and/or zinc may not be listed or contained within an ingredient impact for that particular ingredient. Information pertaining to serving sizes and/or ingredient impacts may be updated in real time utilizing any network methodology as described herein.

Figure 8:
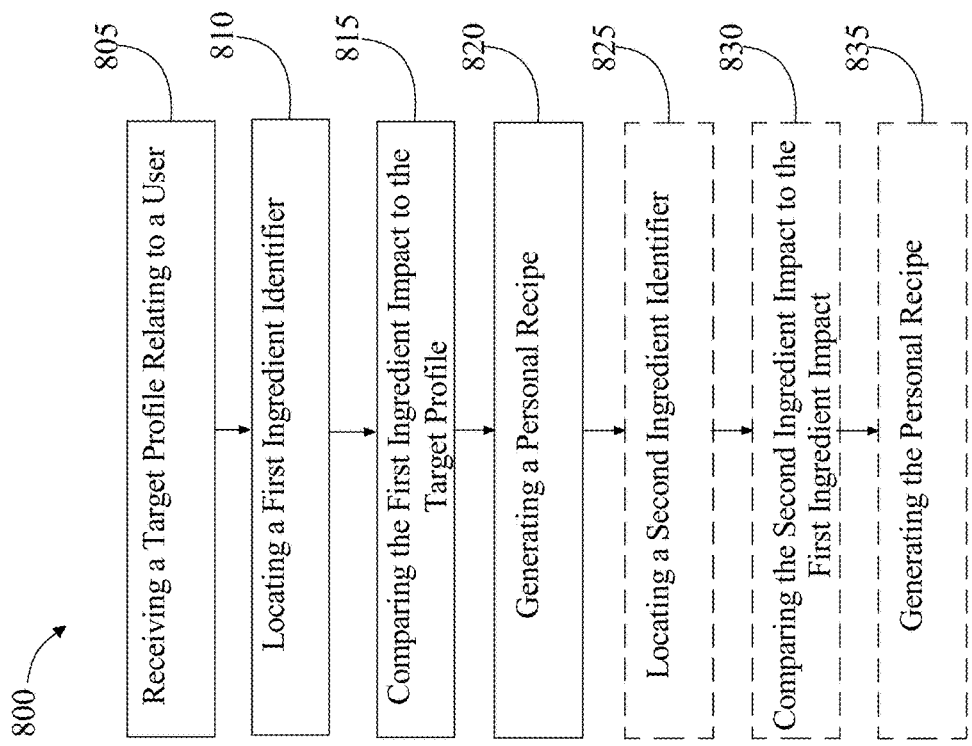
FIG. 8 is a flow diagram illustrating an exemplary embodiment of a method of personal recipe generation.

Referring now to FIG. 8, an exemplary embodiment 800 of a method of personal recipe generation is illustrated. At step 805, computing device 104 receives a target profile 108 relating to a user. Target profile 108 includes any of the target profiles 108 as described above in more detail in reference to FIG. 1. Target profile 108 may include one or more recommended nutrients for a user, such as for example due to a nutrient deficiency an. For instance, and without limitation, a target profile 108 may recommend that a user needs to consume 100 mg of thiamine per day and that the user should not consume more than 2000 mg of sodium per day. In yet another non-limiting example, target profile 108 may include a recommendation for a user to consume 35 grams of fiber, 400 mg of magnesium, and no more than 10 grams of sugar per day. Target profile 108 may identify a nutrient target computed for a measured time interval as described above in more detail. Target profile 108 may be determined using a nutrient anomaly 120. A nutrient anomaly 120 includes any of the nutrient anomalies as described above in more detail in reference to FIG. 1. A nutrient anomaly 120 may indicate an abnormality relating to a user's current nutrient status and/or requirements and may be utilized to generate a target profile 108. For instance and without limitation, a nutrient anomaly 120 may indicate that a user has high levels of b vitamins in the user's body, and as such, the user should consume no more than 500 mg per day of b vitamins. In yet another non-limiting example, a nutrient anomaly 120 may indicate that a user has very low levels of ferritin, and as such a target profile 108 may recommend for the user to consume 100 mg of ferrous sulfate daily in combination with 250 mg of vitamin c per day. Information relating to a nutrient anomaly 120 and/or information utilized to generate a target profile 108 may be stored within user database 112. In an embodiment, a nutrient anomaly 120 may contain a temporal element, including any of the temporal elements as described above in more detail in reference to FIG. 1. In an embodiment, a temporal element may specify how long a nutrient anomaly 120 has been ongoing. In an embodiment, a first nutrient anomaly 120 may be identified as a function of a second nutrient anomaly 120. For instance, and without limitation, a first nutrient anomaly 120 such as a deficiency of copper may be related to a second nutrient anomaly 120 such as an excess of zinc. In yet another non-limiting example, a first nutrient anomaly 120 such as an excess of omega 6 fatty acids may be related to a second nutrient anomaly 120 such as a deficiency of omega 9 fatty acids.

With continued reference to FIG. 8, at step 810 computing device 104 locates in a lexicon of ingredients a first ingredient identifier 124 including a first ingredient impact 132. First ingredient identifier 124 includes any of the first ingredient identifiers 124 as described above in more detail in reference to FIG. 1. First ingredient identifier 124 may identify a first ingredient. Information pertaining to first ingredient identifier 124 and/or ingredients may be contained within ingredient database 128. First ingredient identifier 124 includes a first ingredient impact 132. First ingredient impact 132 specifies nutrients contained within an ingredient. Computing device 104 locates a first ingredient identifier 124 based on information pertaining to a user's preference, which may be contained within user database 112. For instance, and without limitation, a user's preference to consume all animal proteins except for chicken may be utilized to select a first ingredient identifier 124 such as for a filet mignon steak. In yet another non-limiting example, a user's preference to consume a vegetarian diet may be utilized to select a first ingredient identifier 124 such as eggplant. Information pertaining to various ingredients may be stored and contained within ingredient database 128.

With continued reference to FIG. 8, at step 815 computing device 104 compares first ingredient impact 132 to target profile 108. Comparing may include determining how well first ingredient impact 132 meets and/or exceeds the nutritional target contained within target profile 108. For instance and without limitation, computing device 104 may compare first ingredient impact 132 for an ingredient such as cooked spinach, which contains 260 mcg of folate per cup, to a target profile 108 that recommends 200 mcg of folate per day. In an embodiment, computing device 104 may disregard a first ingredient identifier 124 that does not meet requirements contained within a target profile 108. For instance and without limitation, a first ingredient identifier 124 that specifies an ingredient such as a kiwi may not be selected to be included in personal recipe 136 if a target profile 108 specifies that a user should consume no more than 125 mg of Vitamin C per day, and a first ingredient impact 132 for the kiwi indicates that the kiwi contains 65 mg of Vitamin C.

With continued reference to FIG. 8, at step 820, computing device 104 generates a personal recipe 136. Personal recipe 136 includes any of the personal recipes as described above in more detail in reference to FIG. 1. At step 825, computing device 104 may generate personal recipe 136 by locating a second ingredient identifier 144, containing second ingredient impact 148. Second ingredient identifier 144 may be selected using information contained within recipe database 140. For instance and without limitation, recipe database 140 may contain an entry that a first ingredient identifier 124 such as fresh strawberries may be best matched with a second ingredient identifier 144 such as blueberry, blackberry, raspberry, basil, mint, cinnamon, vanilla, and/or cardamom. In such an instance, computing device 104 may select second ingredient identifier 144 from such an entry contained within recipe database 140. Computing device 104 may locate second ingredient identifier 144 by selecting a second ingredient that improves first ingredient impact 132. For instance, and without limitation, computing device 104 may locate second ingredient identifier 144 for an ingredient that enhances absorption and bioavailability of a first ingredient, thereby improving first ingredient impact 132. For example, computing device 104 may locate a second ingredient identifier 144 for an ingredient such as avocado, which may enhance absorption of Vitamin K found in romaine lettuce when both are paired and consumed together. At step 830, computing device 104 compares second ingredient impact 148 to first ingredient impact 132 and target profile 108. Comparing may include determining how second ingredient impact 148 may impact and/or affect first ingredient impact 132. For instance, and without limitation, a second ingredient may not be selected such as when the second ingredient impact 148 may adversely affect a first ingredient impact 132. For example, a first ingredient such as black tea may be adversely affected when combined with a second ingredient such as cow's milk, because the cow's milk may inhibit absorption of phytochemicals contained within black tea, thus adversely affecting first ingredient impact 132. In yet another non-limiting example, a first ingredient such as yogurt may be adversely affected when combined with a second ingredient such as blueberries, because the blueberries may inhibit absorption of calcium contained within the yogurt. At step 830, computing device 104 generates personal recipe 136 using first ingredient identifier 124 and second ingredient identifier 144. Generating personal recipe 136 is performed as a function of first semantic unit and second semantic unit. Computing device 104 may generate personal recipe 136 using a machine learning process 152 as described above in more detail in reference to FIGS. 1-5. Generating personal recipe 136 may include selecting a cooking style, as described above in more detail in reference to FIG. 1. In an embodiment, computing device 104 may select a cooking style using target profile 108. For instance and without limitation, computing device 104 may select a cooking style such as sautéing based on a target profile 108 that contains a recommendation for a user to consume no more than 15 grams of saturated fat per day, as compared to other cooking styles which may create high levels of saturated fat, such as frying.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
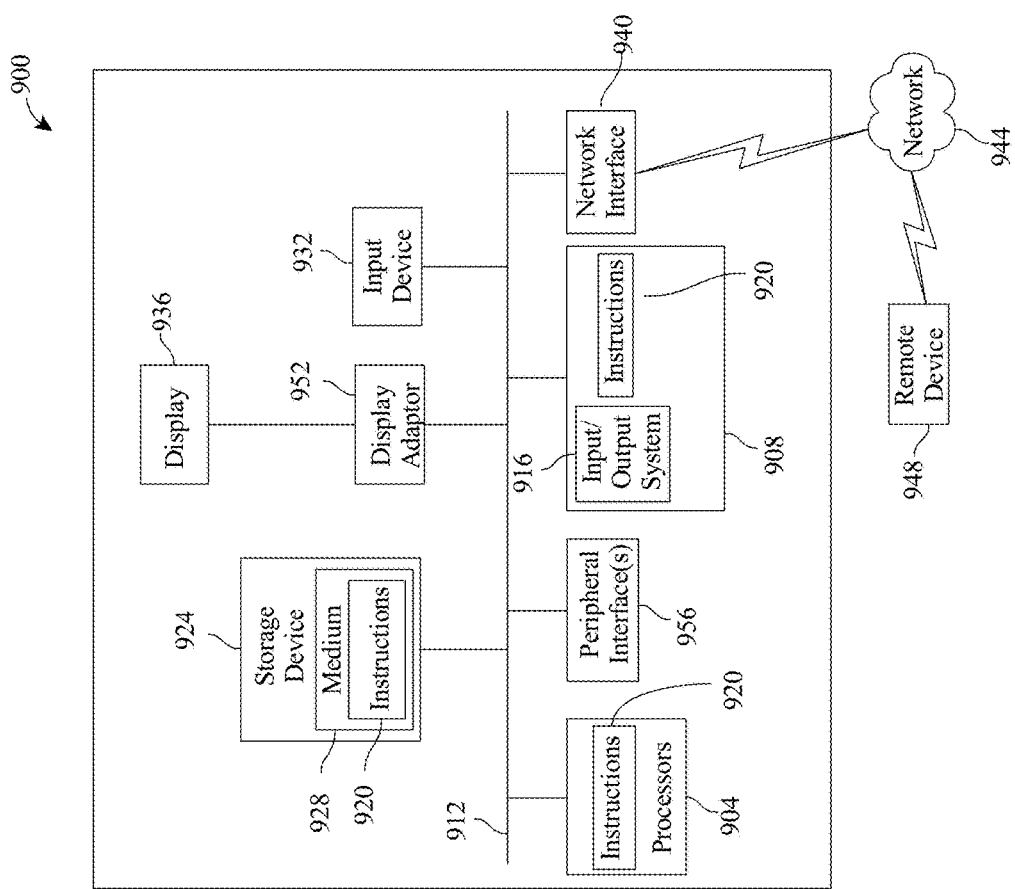
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIRE-WIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for personal recipe generation, the system comprising:
    a computing device, the computing device designed and configured to:
    receive a target profile relating to a user, wherein the target profile identifies a nutrient target computed for a measured time interval;
    locate, in a lexicon of ingredients, wherein the lexicon associates a plurality of ingredient identifiers to a plurality of ingredient impacts and a plurality of semantic units, a first ingredient identifier including a first ingredient impact and a first semantic unit, wherein the first ingredient impact is determined as a function of a user's biological extraction;
    compare the first ingredient impact to the target profile; and
    generate a personal recipe, wherein generating the personal recipe further comprises:
        locating, in the lexicon, a second ingredient identifier wherein the second ingredient identifier includes a second ingredient impact and a second semantic unit;
        comparing the second ingredient impact to the first ingredient impact and the target profile;
        training a machine learning model using training data, wherein the training data correlates a user target profile and a biological extraction of a user to a personal recipe; and
        generating the personal recipe as a function of the machine learning model, wherein, the machine learning model inputs a user target profile and a biological extraction of a user and output a personal recipe.

2. The system of claim 1, wherein the computing device is further configured to:
    identify a nutrient anomaly relating to the user; and
    determine the target profile as a function of the nutrient anomaly.

3. The system of claim 2, wherein the nutrient anomaly includes a temporal element.

4. The system of claim 2, wherein the nutrient anomaly is a first nutrient anomaly, and the computing device is further configured to identify the first nutrient anomaly as a function of a second nutrient anomaly.

5. The system of claim 1, wherein the computing device is further configured to locate the first ingredient identifier as a function of a user preference.

6. The system of claim 1, wherein locating the second ingredient identifier further comprises identifying a second ingredient, wherein the second ingredient improves the first ingredient impact.

7. The system of claim 1, wherein locating the second ingredient identifier further comprises disregarding the second ingredient identifier and locating a third ingredient identifier.

8. The system of claim 1, wherein generating the personal recipe further comprises selecting a cooking style and wherein the cooking style is selected as a function of the target profile.

9. The system of claim 1, wherein the computing device is further configured to generate the personal recipe as a function of a machine learning process, wherein the machine learning process utilizes the target profile as an input, and outputs the personal recipe.

10. The system of claim 9 further comprising training the machine learning process as a function of training data, wherein training data contains a plurality of data entries including a target profile correlated to a personal recipe.

11. A method of personal recipe generation, the method comprising:
    receiving, by a computing device, a target profile relating to a user, wherein the target profile identifies a nutrient target computed for a measured time interval;
    locating, by the computing device, in a lexicon of ingredients, wherein the lexicon associates a plurality of ingredient identifiers to a plurality of ingredient impacts and a plurality of semantic units, a first ingredient identifier including a first ingredient impact and a first semantic unit, wherein the first ingredient impact is determined as a function of a user's biological extraction;
    comparing, by the computing device, the first ingredient impact to the target profile; and
    generating, by the computing device, a personal recipe, wherein generating the personal recipe further comprises:
        locating in the lexicon, a second ingredient identifier, wherein the second ingredient identifier includes a second ingredient impact and a second semantic unit;
        comparing the second ingredient impact to the first ingredient impact and the target profile;
        training a machine learning model using training data, wherein the training data correlates a user target profile and a biological extraction of a user to a personal recipe; and
        generating the personal recipe as a function of the, the machine learning model, wherein the machine learning model inputs a user target profile and a biological extraction of a user and outputs a personal recipe.

12. The method of claim 11, wherein receiving the target profile further comprises:
    identifying a nutrient anomaly relating to the user; and
    determining the target profile as a function of the nutrient anomaly.

13. The method of claim 12, wherein the nutrient anomaly includes a temporal element.

14. The method of claim 12, wherein the nutrient anomaly is a first nutrient anomaly, and the computing device is further configured to identify the first nutrient anomaly as a function of a second nutrient anomaly.

15. The method of claim 11, wherein locating the first ingredient identifier further comprises locating the first ingredient identifier as a function of a user preference.

16. The method of claim 11, wherein locating the second ingredient identifier further comprises identifying a second ingredient, wherein the second ingredient improves the first ingredient impact.

17. The method of claim 11, wherein locating the second ingredient identifier further comprises disregarding the second ingredient identifier and locating a third ingredient identifier.

18. The method of claim 11, wherein generating the personal recipe further comprises selecting a cooking style and wherein the cooking style is selected as a function of the target profile.

* * * * *